United States Patent [19]

Albert

[11] 4,259,583
[45] Mar. 31, 1981

[54] IMAGE REGION SELECTOR FOR A SCANNING X-RAY SYSTEM

[76] Inventor: Richard D. Albert, 317 Hartford Rd., Danville, Calif. 94526

[21] Appl. No.: 35,437

[22] Filed: May 3, 1979

[51] Int. Cl.³ .............................. A61B 6/08; A61B 6/14
[52] U.S. Cl. ........................... 250/416 TV; 250/439 P; 250/508; 250/521; 358/111
[58] Field of Search ............ 250/416 TV, 521, 445 T, 250/439 P, 508; 358/111

[56] References Cited

U.S. PATENT DOCUMENTS

| | | | |
|---|---|---|---|
| 1,164,987 | 12/1915 | Bucky | 250/508 |
| 2,730,566 | 1/1956 | Bartow et al. | |
| 2,777,068 | 1/1957 | Bowser | 250/521 |
| 3,102,957 | 9/1963 | Slauson | 250/508 |
| 3,622,785 | 11/1971 | Irwin et al. | |
| 3,949,229 | 4/1976 | Albert | 250/401 |
| 4,031,395 | 6/1977 | LeMoy | 250/360 |

Primary Examiner—Alfred E. Smith
Assistant Examiner—T. N. Grigsby
Attorney, Agent, or Firm—Phillips, Moore, Weissenberger, Lempio & Majestic

[57] ABSTRACT

Examination of dental patients or other subjects (14) with a radiographic system (11) having a scanning X-ray source (17) and a collimator (58) with a plurality of passages (62) for directing X rays to a detector (51) is facilitated by an image region selector (12) which is separate from the source. The selector (12) includes the detector (51) and means (64) defining the collimator position at which the collimator passages (62) are directed towards the detector (51). The selector (12) may be positioned and independently supported, to establish the region to be imaged, prior to the time that the relatively heavy and bulky X-ray source (17) is maneuvered into position for making the examination.

19 Claims, 6 Drawing Figures

FIG_5

FIG_6

IMAGE REGION SELECTOR FOR A SCANNING X-RAY SYSTEM

TECHNICAL FIELD

This invention relates to radiography and more particularly to apparatus for defining the region of a subject to be examined by a scanning X-ray system in which X rays from a moving origin point are transmitted to detection means at the other side of the subject to produce signals from which an image may be produced.

BACKGROUND OF THE INVENTION

U.S. Pat. No. 3,949,229 entitled, X-ray Scanning Method and Apparatus, issued Apr. 6, 1976 to the present applicant, discloses a scanning X-ray system for producing high quality radiographic images, instantaneously if desired, with substantially less radiation dosage of a subject than is required by older radiographic techniques which use X-ray film or florescent screens.

The scanning X-ray system of U.S. Pat. No. 3,949,229 includes an X-ray source generating a moving X-ray origin point which is swept along successive spaced apart scan lines of a raster pattern area. A radiation detector is situated at the opposite side of a subject to be examined. Output signals from the detector modulate the electron beam intensity within a cathode ray display tube such as an oscilloscope, a television receiver or the like. The beam sweep raster pattern of the display tube is synchronized with that of the X-ray source to produce an instantaneous visible radiographic image of internal regions of the subject. The output signals of the detector together with the sweep frequency signals from the X-ray source may also be stored on magnetic tape or the like for later reproduction of the image.

A scanning X-ray system of the particular kind disclosed in prior U.S. Pat. No. 3,949,229 is capable of producing an image without using a collimator or X-ray focusing device between the X-ray source and the detector but as a practical matter usage of a collimator is desirable under many circumstances. The collimator is typically a body of X-ray absorbent material which is situated between the X-ray source and the subject and which has rows of small radiation transmissive passages which are directed towards the detector.

The collimator reduces radiation dosage of the subject by suppressing X rays which are not directed toward the small detector and which therefore could not contribute useful information to the image. The collimator also enhances image clarity by reducing secondary X-ray production at random origin points within the subject.

The scanning X-ray system of the above identified U.S. patent was designed primarily for medical and dental examinations although it is also useful for other purposes such as in the quality checking of metallurgical castings or other manufactured parts. In some of these usages, and very notably in connection with dental examinations, positioning of the scanning X-ray apparatus in preparation for an examination of a subject may be time consuming and may require complicated and taxing operations.

To select and define the region of the subject which is to appear in the image, a radiation detector must be carefully positioned and then fixedly supported at one side of the region which is to be examined and the collimator must be positioned and then supported at the other side in an orientation at which the collimator passages are directed towards the detector.

The particular form of scanning X-ray system described in prior U.S. Pat. No. 3,949,229 uses one or more detectors which are very small in relation to the X-ray origin point raster area at the X-ray source. This requires use of a focusing collimator in which the radiation transmissive passages are convergent towards a distant focal point which may be the location of the detector. Consequently, the detector and collimator must not only be precisely positioned relative to the subject but also with respect to each other. As the passages of the collimator are convergent, there is a specific alignment and a particular spacing or narrow range of spacings which must be established between the detector and the collimator in order that X rays which are transmitted through the different portions of the collimator will all be intercepted by the small detector.

Some other forms of scanning X-ray system, such as those disclosed in prior U.S. Pat. No. 2,730,566 issued Jan. 10, 1956 to J. B. Bartow, et al and entitled, Method and Apparatus for X-ray Fluoroscopy, employ a bulky detector at least as broad as the X-ray raster pattern area of the X-ray source. Consequently, such systems may use a non-focusing collimator in which the radiation transmissive passages are parallel rather than being convergent. Because of the absence of a finite focal point, the particular matter of spacing of the detector from the X-ray source may not be so critical in such systems but the other positioning and orientation problems discussed above, in arranging the detector and collimator to image a selected region, can still be encountered.

Difficulties in positioning and then supporting the detector and collimator in a selected relationship to the subject and also in a selected relationship to each other tend to be particularly pronounced in connection with dental X-ray examinations since the detector together with means for transmitting the X-ray count signals from the detector must often be situated inside the mouth of the dental patient.

In the scanning X-ray systems as disclosed in the above identified prior U.S. patents, the collimators are usually secured to the face of the X-ray source itself. Positioning of the collimator for image selection therefore requires careful maneuvering of the relatively bulky and heavy X-ray source itself. The detector is movable independently of the source and is supported by essentially independent means. Consequently, the supports and positioning means do not inherently establish the detector and collimator positions, alignments and spacings necessary to image a selected region of the subject. These must be arrived at by trial maneuverings of both the detector and the heavy collimator-source assembly relative to the subject and relative to each other.

The complications of positioning and supporting the apparatus in preparation for a radiographic examination are greatly alleviated by a source, collimator and detector construction disclosed in applicant's copending U.S. application Ser. No. 803,077 filed June 3, 1977 and entitled, Scanning Radiographic Apparatus and Method. In that construction, both the collimator and the detector are attached to the face of the X-ray source itself forming a unitized assembly in which the necessary alignments and spacings of the collimator relative to the detector are inherently fixed. More specifically, the detector is situated in a removable rigid probe which extends forwardly from the face of the source to maintain the detector at the point at which it intercepts the X rays which are transmitted through the passages of the collimator. Thus, in setting up for an examination, the dentist, dental technician or other operator need not be concerned about positioning or orientation of the detector relative to the source and collimator but instead simply maneuvers all three components as a unit relative to the subject to select the region of the subject which is to appear in the image.

Further simplification of the process of setting up for an X-ray examination would be highly desirable. Precise maneuvering and positioning of the unitized X-ray source, collimator and detector probe described above can be somewhat taxing under some circumstances, primarily because of the inclusion of the heavy and bulky X-ray source in the unit. In the case of dental examinations where the protruding detector probe extends into the mouth of the patient, inprecise or undesirably abrupt movements of the unit can cause patient discomfort or other undesirable effects. Also, the presence of the bulky X-ray source in front of the patient's face during the image selection process restricts visibility of the patient's dentition. Somewhat similar problems may be encountered in usage of such apparatus for certain nondental applications. Where the probe must be maneuvered into a constricted passage within a metallurgical casting, for example, inadvertent abrupt movements of the heavy unitized apparatus can result in damage or breakage of the detector probe.

Setting up of a scanning X-ray system of this general kind for dental examinations and for certain other radiographic operations as well would be facilitated by reducing the bulk and weight of the apparatus which the operator must maneuver, position and then fixedly support in order to select and fix the region of the subject to be imaged.

DISCLOSURE OF INVENTION

The present invention is directed to overcoming one or more of the problems as set forth above.

In one aspect of this invention an X-ray image region selector assembly facilitates operation of a scanning X-ray radiographic system of the type in which an X-ray source and a collimator are disposed at one side of the region to be imaged, the source having a moving X-ray origin point which is swept through a raster pattern area and the collimator having a plurality of passages for transmitting X rays from different portions of the raster pattern area towards a detector situated at the opposite side of the region to be imaged.

The image region selector is maneuverable and supportable independently of the X-ray source and includes detector support means for supporting the detector at a selected position relative to the subject prior to movement of the X-ray source into position. The image region selector further includes collimator positioning means defining a predetermined collimator position which is spaced apart from the detector and at which the collimator passages are directed towards the detector, the collimator positioning means being secured to the detector support means.

As the image region selector carrying both the detector and collimator positioning means in fixed optimum relationship to each other is a separable component from the X-ray source, the selector may easily be maneuvered and positioned to select the region of the subject to be imaged and may then be independently supported at the selected position while the relatively bulky and heavy X-ray source itself is brought into position to seat against the selector and to direct X rays towards the detector through the collimator. Maneuvering of the X-ray source is made much simpler and straight forward as the image region has been preselected and preestablished.

In a dental X-ray system, the image region selector assembly can be sufficiently light in weight to be supportable in a selected relationship to the patient's dentition by being clamped in the teeth of the patient although other support means may also be used.

In one specific aspect of the invention the collimator may be secured to the face of the X-ray source in position to be brought into engagement with the collimator positioning means of the image region selector as the source itself is moved into position. In another aspect of the invention the collimator may be a fixed component of the image region selector rather than being attached to the X-ray source.

BEST MODES OF PRACTICING THE INVENTION

Figure 1:
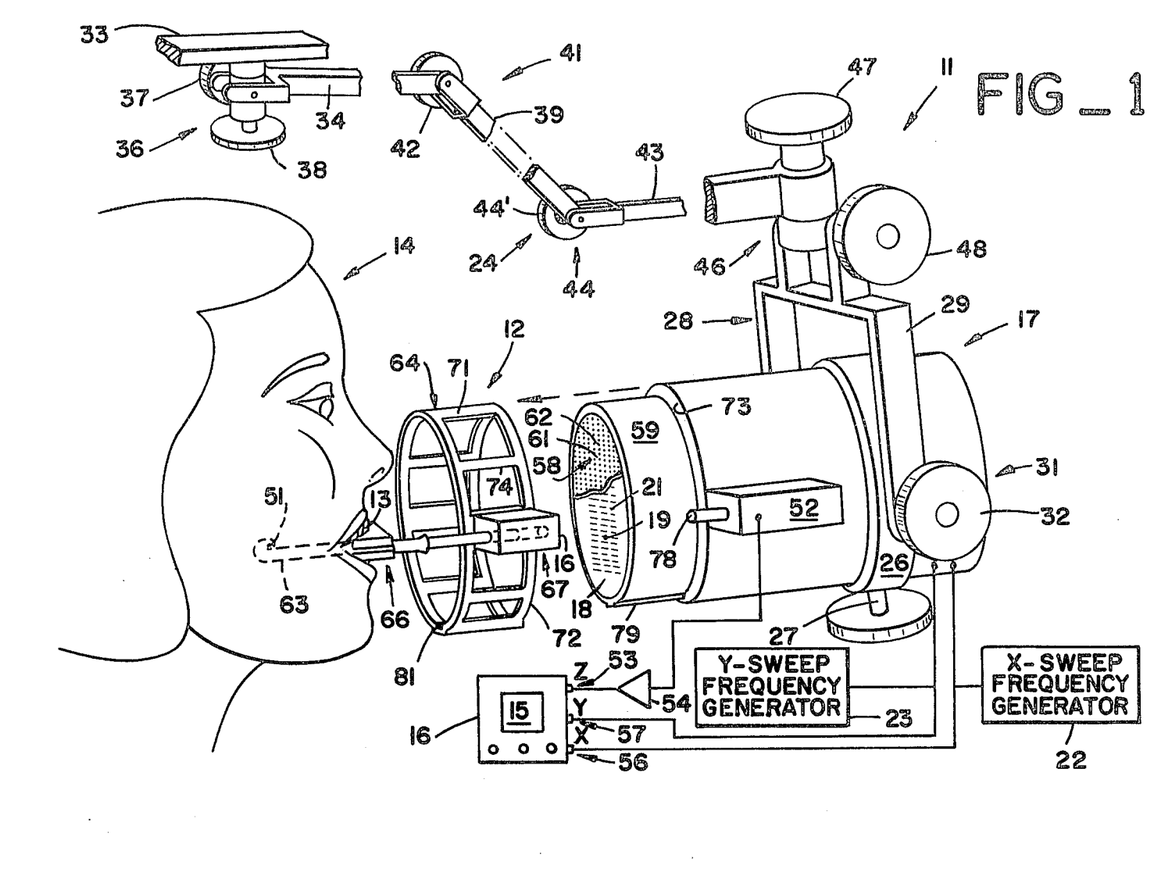
FIG. 1 is a perspective view of a dental X-ray system for producing an instantaneous radiographic image of a selected region of a patient's dentition, the system including an image region selector means in accordance with a first embodiment of the invention.

Referring initially to FIG. 1 of the drawings, a scanning X-ray system 11 having an image region selector unit 12 in accordance with the invention may be used to generate radiographic images of the teeth 13 of a dental patient 14 on the screen 15 of an X-Y display device which may typically be a television receiver 16 or an oscilloscope or other form of cathode ray tube display. The system 11 may also readily be adapted to medical examinations of other portions of the human body or to the imaging of internal regions of inanimate objects.

The system 11 includes a scanning X-ray source 17 which may be of the form disclosed in my above identified prior U.S. Pat. No. 3,949,229 and which therefore will not be described in detail except for certain aspects which will be briefly reviewed to facilitate an understanding of the coaction of the present invention with the source. In particular, the source 11 has an anode or target plate 18, defining a raster pattern area, against which an electron beam is impacted to produce an X-ray origin point 19. The electron beam is swept in a raster pattern to cause the X-ray origin point 19 to move successively along parallel scan lines 21, the spacing of the scan lines being exaggerated in FIG. 1 for clarity of illustration. The rate of progression of the origin point 19 along the successive scan lines is determined by an X-sweep frequency generator 22 coupled to the X-ray source while the rate of progression of the origin point from one scan line to the next is determined by a Y-sweep frequency generator 23 also coupled to the source and which has a lesser output frequency than the X-sweep frequency generator 22.

Source support means 24 enables maneuvering of the X-ray source 17 into a selected position relative to the subject 14 and further provides for immobilizing the source at the selected position. For dental usage as in this example, it is preferable that the support means 24 enable movement of the source 17 vertically and sidewardly and forwardly and backwardly relative to the subject 14 and the source should be tiltable about a transverse axis and pivotable about a vertical axis. Where the embodiment of the invention depicted in FIG. 1 is employed, the source 17 should also be capable of being turned angularly about its own center line.

A suitable support means 24 for this purpose may include an annular support band 26, encircling the source 17, which enables rotation of the source about its central axis. To immobilize the source 17 at a selected rotational orientation, a handwheel operated set screw 27 is provided at band 26 to selectively exert clamping pressure against the source.

A support fork 28 has a pair of arms 29 which extend downwardly at opposite sides of the source and which are coupled to band 26 at pivot joints 31 of the type which can be locked at a selected angulation by turning another handwheel 32.

Fork 28 is in turn coupled to a stationary support 33 through multijointed linkage which in this example includes a first arm 34 attached to the support 33 through a lockable double pivot joint 36 of the type which allows the arm to be pivoted both horizontally and vertically and which has handwheels 37 and 38 for immobilizing the arm at a selected orientation.

Arm 34 is coupled to an intermediate support arm 39 through a pivot joint 41 which has a horizontal pivot axis and which may be clamped at a selected angulation by turning still another handwheel 42. The other end of intermediate arm 39 is pivotally coupled to a third arm 43 through still another clampable pivot joint 44 also having a horizontal pivot axis. The opposite end of the third arm 43 couples to fork 28 through another lockable double pivot joint 46 capable of pivoting motion about both a horizontal and vertical axis but which may be clamped at a selected angulation by turning handwheels 47 and 48. Thus after release of the several lockable joints of the support means 24, X-ray source 17 may be shifted in any direction relative to the dental patient 14 and may also be tilted and rotated. The source 17 may then be immobilized at a selected position and orientation by tightening the several handwheels 27, 32, 37, 38, 42, 44', 47 and 48.

In some instances the complex support means 24 described above may be simplified by mounting the X-ray source 17 and some or all of the associated circuit components on a mobile cart having wheels and brakes. Those portions of the support linkage which provide for horizontal movement of the source 17 and for pivoting of the source about a vertical axis may then be eliminated as such motions can be accomplished simply by movements of the cart.

To produce the radiographic image at the screen 15 of television receiver 16, a small X-ray detector element 51 is situated on the opposite side of the region to be imaged, the region in this example being a selected portion of the teeth 13 of the dental patient 14. Any of various forms of radiation detector elements 51 may be used, the detector in this example being a small scintillator crystal of the type which produces optical output signals in response to X rays. Means 63 to be hereinafter described in more detail transmits the optical signals to a photomultiplier tube 52 or a photodiode secured to the side of the X-ray source 17 and which converts such signals to electrical signals.

The electrical output signals of the photomultiplier tube 52 are transmitted to the Z or intensity signal terminal 53 of television receiver 16 through an amplifier 54. The X- and Y-sweep frequency terminals 56 and 57 of the television receiver 16 receive the same sweep frequencies, from X-sweep frequency generator 22 and Y-sweep frequency generator 23 respectively, that are provided to the X-ray source 17 itself. Thus the electron beam raster scanning pattern of receiver 16 is synchronized with that of the X-ray source 17 while the intensity of the electron beam of the receiver varies in accordance with the X-ray flux received at detector 51 at successive times in the scanning action. Thus the brightness of each successive point in the image appearing on screen 15 is determined by the degree of X-ray absorption which occurs along a line extending from the X-ray origin point 19 to the detector 51 at a corresponding point in the raster pattern at the X-ray source and a visible radiographic image of the scanned region of the subject is produced at screen 15.

Figures 2, 3, 4:
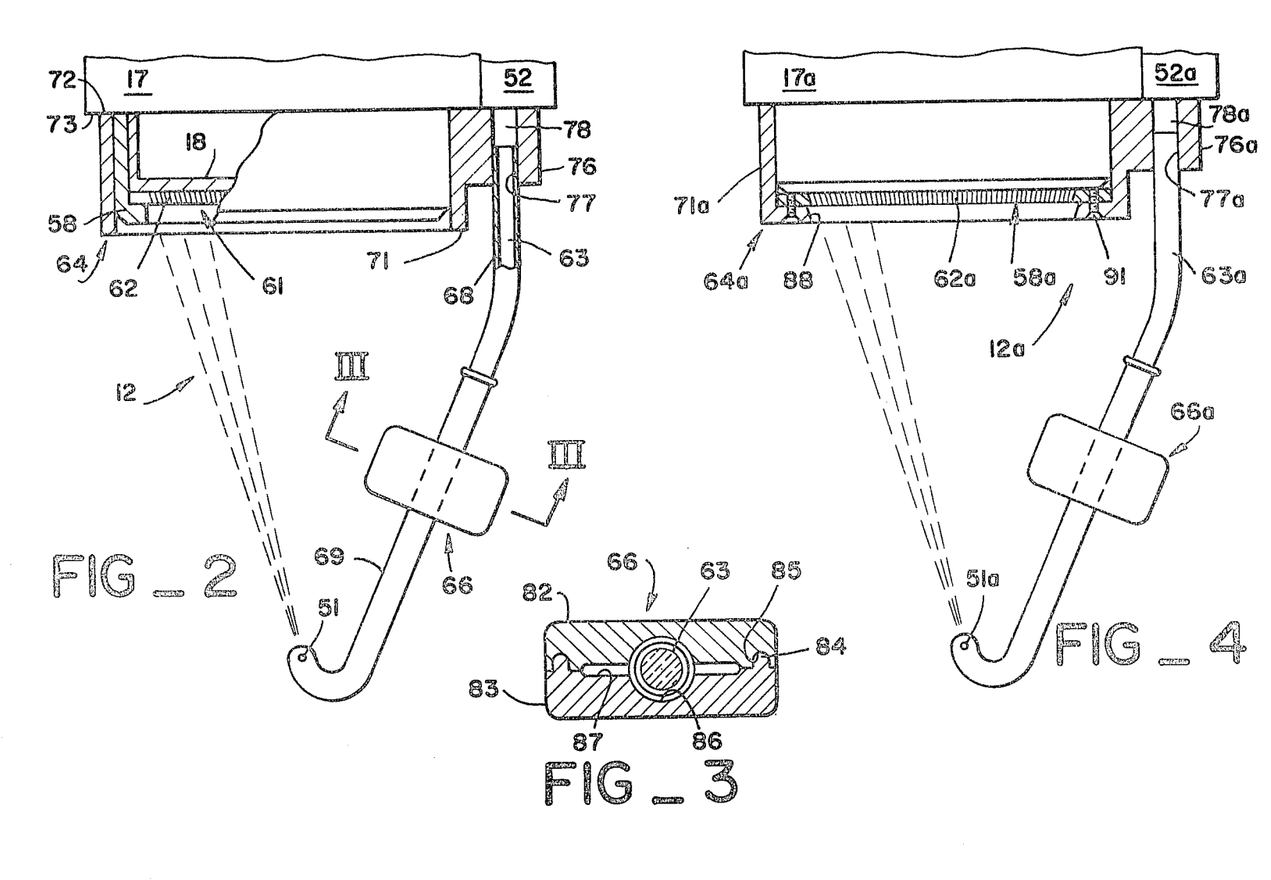
FIG. 2 further depicts the image region selector component of the system of FIG. 1, a portion of the apparatus being shown in section.
FIG. 3 is a cross-sectional view taken along line III—III of FIG. 2.
FIG. 4 depicts a second embodiment of the image region selector also with a portion of the apparatus being shown in section.

To enhance image clarity and to further reduce radiation dosage of the subject 14, a collimator 58 is situated between the X-ray source 17 and the region 13 of the subject which is to be imaged. The collimator is secured to the face of the X-ray source in this particular embodiment and is of the focusing form in this example since the detector 51 is smaller than the raster pattern area through which X-ray origin point 19 is swept. The collimator body 61, supported by an annular mounting member 59, has a circular configuration to conform with the circular configuration of this particular X-ray source 17 and is composed at least in part of a radiation absorbent material of which lead, copper, molybdenum or tungsten among other metals, are examples. The collimator body 61 is transpierced by rows of radiation transmissive passages 62 which, as may be seen by referring to FIG. 2 are convergent so that each passage is directed toward a single focal point situated outwardly from the collimator along the center line thereof and which is the position of the small detector 51 in this example when the X-ray source is being operated. In systems where the detector 51 is larger, the focal point may be in front of the detector 51 or behind it provided that the detector is proportioned to intercept all X rays transmitted through any of the collimator passages 62. In systems where the detector is as large as the raster pattern area of the X-ray source 17, a nonfocusing collimator having nonconvergent or parallel passages may be used.

Referring again to FIG. 1, the collimator 58 acts to absorb X rays emitted from origin point 19 which are not directed toward the detection element 51 but which would otherwise increase the radiation dosage of the subject without contributing useful information to the image. The collimator 58 also enhances image clarity by reducing the production of secondary X rays at random points within the subject which secondary X rays, if intercepted by the detector 51, would cause fogging in the image. The effectiveness of the collimator 58 for both of these purposes is increased if the collimator is formed with a very large number of passages 62 of minute cross-sectional area and close spacing. In the present context, it is also advantageous if the weight of the collimator is minimized. While the collimator 58 may be of known construction, produced for example by careful drilling of the passages 62 through a plate of radiation absorbent metal, the above described characteristics are best provided by utilizing a laminated collimator construction of the kind described in copending U.S. Patent Ser. No. 035,733 of the present applicant, filed concurrently with this application and entitled, Laminate Radiation Collimator and Method of Manufacture Thereof.

Considering now one suitable detailed construction for the image region selector unit 12, the detector 51 is disposed within a first end of a probe like detector support 63 which has collimator positioning means 64 at the opposite end to define the collimator position at which the convergent passages 62 of the collimator are directed at the detector. The image region selector 12 also has support means 66 for holding the selector unit in a fixed orientation relative to the subject 14 prior to the time that the X-ray source 17 is advanced into position for an examination, the support means being a bite block grippable by the teeth of the dental patient in this embodiment. To transmit X-ray count signals from detector 51 to photomultiplier tube 52 at the X-ray source, connector means 67 of the image selector engage with the photomultiplier as the source is seated at the collimator positioning means 64.

As the detector 51 of this embodiment is a scintillator which produces visible light in response to X rays, the detector support probe 63 is an optical light pipe formed of light transmissive plastic or fiber optical material. Referring again to FIG. 2, light pipe probe 63 is enclosed by a tubular protective sleeve 68 of aluminum or other material which is opaque to light and of low X-ray absorbency. A disposable sterilized sheath 69 is fitted on at least that portion of the probe 63 that enters the mouth of the dental patient, preferably by placing a rolled sheath 69 against the end of the probe 63 and then by unrolling the sheath along the probe for the desired distance. Sheath 69 is replaced at each subsequent usage of the system.

Collimator positioning means 64 is an annular basket 71 of lightweight plastic material having an inside diameter conforming to the outside diameter of the collimator 58 in order to receive the collimator as the X-ray source is advanced into position for a dental examination. An annular surface 73 of the X-ray source seats against an end surface 72 of basket 71 when the X-ray source and collimator are at the position at which the collimator passages 62 are directed towards detector 51. To provide the operator with greater visibility of the patient's teeth 13 while positioning the image region selector 12 and to reduce the weight of the selector, broad openings 74 are provided in the sidewall of basket 71.

Referring to FIGS. 1 and 2 in conjunction, the collimator positioner basket 71 is secured to the detector support probe 63 at a connector block 76 at the side of the basket. The end of probe 63 extends partway into a passage 77 in the connector block and is secured to the block by an adhesive or by other suitable means. To transmit the optical signals from detector 51 to photomultiplier tube 52, a light pipe stub 78 extends forwardly from the photomultiplier tube in position to enter connector block passage 77 as the forward end of the X-ray source is advanced into the basket 71. Light pipe stub 78 is of just sufficient length to contact the end of probe 63 within passage 77 when surface 73 of the X-ray source seats against end surface 72 of the basket 71. To assure good transmission of signals, the end surfaces of both probe 63 and light pipe stub 78 may be coated with optical grease.

To avoid possible damage to the light pipe stub 78 from misalignment as the X-ray source is being brought into position, the light pipe stub 78 is situated a short distance behind the face of the collimator 58 and X-ray source 17. Thus a forward portion of the X-ray source including the collimator has already entered basket 71 to establish the proper alignments, before the light pipe stub 78 begins to enter the passage 77 of the connector block. To assure that the angular relationship of the X-ray source 17 and basket 71 are correct at the time that the stub 78 enters connector passage 77, a linear key embossment 79 is formed along the outer surface of the forward portion of the source and enters a conforming key slot 81 in the inner wall of basket 71.

Probe 63 is appropriately curved, between connector block 76 and the detector 51, to locate the detector at the focal point of the collimator 58 while the probe itself remains outside of the image region. The distal end of the probe 63 curves backward for a small distance so that the material of the probe itself is not situated between the detector 51 and the collimator 58.

Referring now to FIGS. 2 and 3 in conjunction, support means 66 for the image region selector 12 for dental usage consists of upper and lower bite blocks 82 and 83 respectively of substantially rectangular configuration and of suitable size for insertion between the teeth 13 of the dental patient. Lower bite block 83 is formed with resilient ribs 84 which enter conforming slots 85 on the lower surface of the upper bite block 82 to enable the two bite blocks to be snapped together with the probe 63 extending between the two blocks through a passage 86 formed by grooves in the adjacent surfaces of the two blocks. A broader, shallow groove 87 is also provided in the abutting surfaces of the two blocks 82 and 83 at each side of groove 86 and the blocks are made of a deflectable material such as rubber or any of various moderately flexible plastics so that the patient's teeth may exert pressure on the probe 63 through the bite blocks. Thus the image selector unit as a whole may be supported and fixed in a selected position relative to the dental patient's teeth by oral clamping pressure on the bite blocks.

OPERATION OF THE EMBODIMENT OF FIGS. 1 TO 3

In use, with reference to FIG. 1, X-ray source 17 is initially situated away from the immediate vicinity of the dental patient 14. A new sterile sleeve 69 is disposed on the end of the probe 63 of the image region selector 12 and the bite blocks 82 and 83 are then snapped into place on the probe, over the sleeve, by forcing ribs 84 into slots 85. The outer end of the probe 63 including a portion of the bite blocks 82 and 83 is then inserted into the mouth of the patient 14. The dentist or dental technician then positions the image region selector 12 so that the portion of the teeth 13 of the patient which is to be imaged is situated between detector 51 and basket 71. For this purpose, the selector 12 may be maneuvered into any of various lateral orientations relative to the face of the patient 14. By rotating probe 63 within bite blocks 82 and 83 the elevation of the detector 51 and collimator positioning basket 71 may be raised and lowered. The degree of magnification in the image may be adjusted by sliding probe 63 longitudinally relative to the bite blocks 82 and 83. The operator may readily view the patient's mouth during these operations through the openings of basket 71.

When the region of the patient's teeth to be imaged has been selected in this manner the patient is instructed to exert clamping pressure on the bite blocks 82 and 83. This immobilizes the image region selector 12 relative to the teeth 13 and thereby fixes the region to be imaged.

After releasing the several handwheel clamped joints 36, 41, 44, 46 and 31 of the X-ray source support linkage 24, the X-ray source 17 is then aligned with basket 71 and advanced into the basket until surface 73 seats against the end surface 72 of the basket which movement locates the collimator 58 at the position where the convergent collimator passages 62 are directed at the detector 51. At the point where the forward end of X-ray source 17 is about to enter basket 71, the source may be rotated within mounting ring 26 to bring key 79 into alignment with key slot 81 of the basket thereby assuring that an angular relationship is established at which light pipe stub 78 will enter passage 77 of the image region selector.

With the X-ray source 17 positioned and seated in the image region selector 12, the several handwheels 37, 42, 44', 47, 48, 32 and 27 of support linkage 24 are turned to immobilize the linkage and thereby hold the X-ray source at the selected position. At this point the support linkage 24 aids the patient 14 in supporting the unit 12.

It is preferable, although not essential, that the subject 14 and the components of the X-ray system 11 be arranged so that the vertical axis about which the source 17 may be pivoted during horizontal movements of the source, which axis is defined by pivot joint 36 in FIG. 1, be located to pass through or close to the position of the distal end of probe 63. Thus in the example of FIG. 1 pivot joint 36 is directly above the head of the dental patient 14. Such an arrangement minimizes patient discomfort if the source 17 should be inadvertently swung horizontally while the probe 63 is inside the patient's mouth as it reduces the amount of lateral displacement of the probe which accompanies such movements of the source.

X-ray source 17 may then be operated as described above and in more detail in prior U.S. Pat. No. 3,949,229 to generate the desired radiographic image on the screen 15 of display means 16. Thereafter the several handwheels of support linkage 24 may again be turned to unlock the joints in the linkage after which the X-ray source 17 may be withdrawn from basket 71. The image region selector 12 may then be repositioned for an additional imaging operation or may be withdrawn from the mouth of the patient.

DESCRIPTION OF SECOND EMBODIMENT

In the example of the invention described above, the collimator 58 is secured to the X-ray source 17 and the image region selector 12 includes means 64 which establishes the collimator position at which X rays emitted from the collimator will converge at detector 51. Alternately, as depicted in FIG. 4, the collimator may be secured within the image region selector 12a in permanent engagement with the positioning means 64a rather than being attached to the X-ray source.

In the embodiment of FIG. 4, the probe 63a, bite block support means 66a and output signal connector block 76a may all be similar to the corresponding portions of the previously described embodiment. The end of basket 71a closest to the detector 51a has an inwardly extending annular shelf 88 against which the collimator 58a is secured by screws 91.

Figure 5:
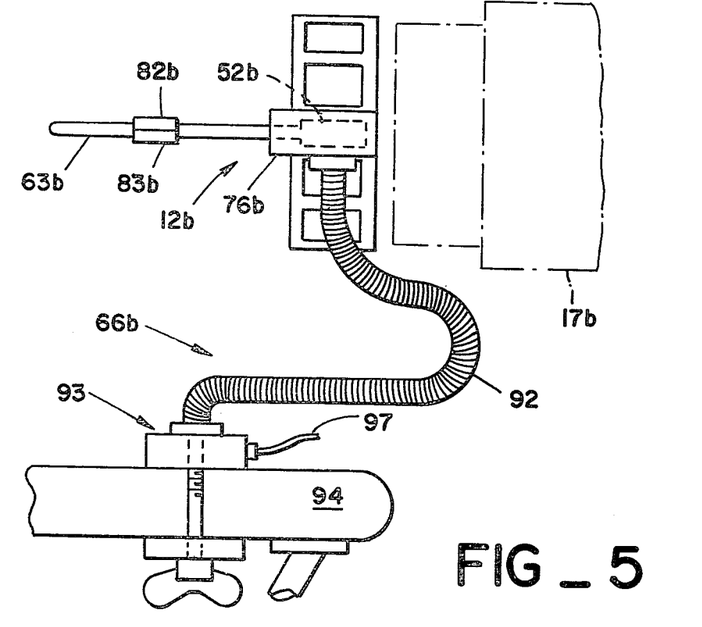
FIG. 5 is a side view of a third embodiment of the image region selector.

Operation of the second embodiment of FIG. 5 may be similar to that of the embodiment of FIGS. 1 to 3 as previously described.

DESCRIPTION OF THIRD EMBODIMENT

In both embodiments of the invention described above, the image region selector 12, 12a is supported by the dental patient's teeth at least prior to the time that the X-ray source 17 is moved into engagement with the selector. Alternately, as shown in FIG. 5, the image region selector unit 12b may be provided other support means 66b which do not depend on assistance from the dental patient.

The image region selector 12b and the X-ray source 17b of the embodiment of FIG. 5 may be similar to the corresponding components of either of the previously described embodiments except that the photomultiplier tube 52b or the like which converts the optical signals received through probe 63b to electrical signals is disposed within connector block 76b of the selector unit 12 rather than being mounted on the source 17b. This avoids the need for establishing a precise angular relationship between the basket 71b and the source 17b at the time that the source is advanced into the basket. As there is no light pipe stub which must enter into connector block 76b at that time, as in the previously described embodiments, the key and key slot means provided on the previously described embodiments, to assure a specific angular orientation of the source relative to the basket, need not necessarily be provided on the embodiment of FIG. 5.

While other forms of support means 66b may also be used, the means 66b in this example includes a multijointed, semi flexible gooseneck element 92 of the known type which may be forcibly bent into a variety of configurations and which then retains the selected configuration until it is again forced into some other selected position. Alternately, a more complex support linkage, of the type hereinbefore described for supporting the X-ray source itself, may also be used.

In this example, gooseneck 92 has one end secured to connector block 76b and an opposite end secured to a releasable clamp 93 which may be fastened to any suitable nearby support such as the arm 94 of a dental chair. Electrical conductors 96 for communicating photomultiplier tube 52b with the previously described circuitry may extend through the hollow gooseneck 92.

While bite blocks 82b and 83b are no longer needed on probe 63b for the purpose of supporting the image region selector 12b, such means may still be provided in some usages to assist in immobilizing the dental patient's head.

Operation of the embodiment of FIG. 5 may be similar to that of the previously described embodiments except that the image region selector 12b is self-supported at the selected position relative to the subject through support means 66b.

DESCRIPTION OF FOURTH EMBODIMENT

Figure 6:
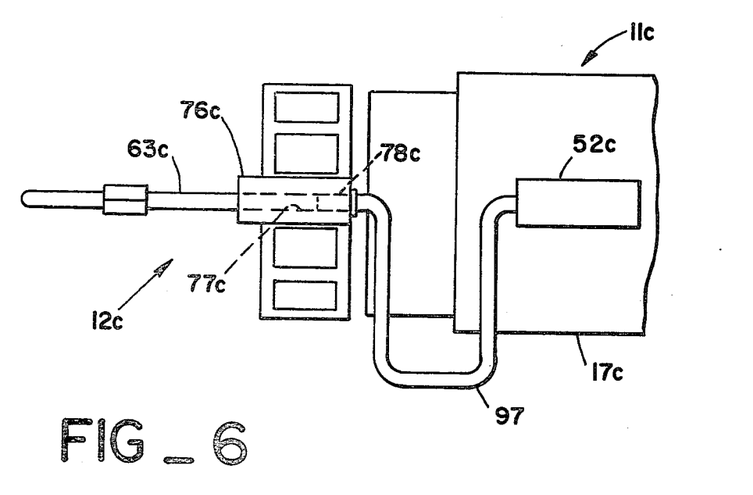
FIG. 6 is a side view of a fourth embodiment of the image region selector.

In the modification of the scanning X-ray system 11c depicted in FIG. 6 it is unnecessary to assure an exact rotational orientation of the X-ray source 17c relative to the image region selector 12c as is required in the first embodiment described above. Unlike the third embodiment described above, which is also free of that requirement, the modification of FIG. 6 allows the photomultiplier tube 52c to be mounted on the X-ray source 17c rather than being attached to the image region selector.

Components of the scanning X-ray system 11c of FIG. 6 may be similar to the corresponding parts of the first embodiment described with reference to FIG. 1 except for modification of the coupling of light pipe stub 78 to the photomultiplier tube 52 and except in that the key 79 and keyway 81 and angular adjustment means 26, 27 at the X-ray source 17 are not required.

In particular, light pipe stub 78c of the embodiment of FIG. 6 is not mounted directly on the photomultiplier tube 52c but is instead physically and optically coupled thereto through a flexible fiber optic cable 97.

The embodiment of FIG. 6 may be operated in a manner similar to the operation of the previously described embodiments except that it is not necessary to be concerned about the angular orientation of the X-ray source 17c relative to that of the image region selector 12c as the source is being advanced into engagement with the selector. After the X-ray source 17c has been seated in the image region selector 12c, light pipe stub 78c is inserted into the passage 77c of connector block 76c of the selector to optically couple to the end of probe 63c and the X-ray examination may then proceed. Where necessary, detent means may be provided in the connector block 76c to assure retention of the light pipe stub 78c in passage 77c.

Other aspects, objects and advantages of this invention can be obtained from a study of the drawings, the disclosure and the appended claims.

I claim:

1. An image region selector for a scanning X-ray radiographic system in which an X-ray source and a collimator are disposed at one side of a region to be imaged, the source having a moving X-ray origin point which is swept through a raster pattern area and the collimator having a plurality of passages for transmitting X rays from different portions of said raster pattern area towards said region to be imaged, and in which at least one radiation detector is disposed at the opposite side of said region in the path of said X rays which are transmitted through said collimator passages, wherein the improvement comprises:
   detector support means for supporting said detector at a selected position at said opposite side of said region prior to movement of said X-ray source into position for producing the desired image data,
   collimator positioning means for defining a predetermined collimator position which is spaced apart from said detector and at which said collimator passages are directed towards said detector, said collimator positioning means being secured to said detector support means in a predetermined spatial relationship to said detector, and
   selector support means for immobilizing said image region selector at a selected position and orientation relative to said region to be imaged, said selector support means being independent of said X-ray source in order to support said selector prior to movement of said X-ray source into position for making a radiographic image of said region.

2. An image region selector as defined in claim 1 wherein said collimator is secured to said collimator positioning means of said selector.

3. An image region selector as defined in claim 1 wherein a first portion of said detector support means has a configuration suitable for insertion into the mouth of a dental patient and wherein said selector support means includes means for enabling said dental patient to immobilize said selector relative to the teeth of said patient.

4. An image region selector as defined in claim 3 wherein said selector support means includes means for facilitating clamping of said first portion of said detector support means between the teeth of said dental patient.

5. An image region selector as defined in claim 3 further including means for receiving and engaging a portion of said X-ray source to enable said selector to be at least partially supported by said X-ray source after movement of said X-ray source into position for making a radiographic image of said region.

6. An image region selector for a scanning X-ray radiographic system in which an X-ray source and a collimator are disposed at one side of a region to be imaged, the source having a moving X-ray origin point which is swept through a raster pattern area and the collimator having a plurality of passages for transmitting X rays from different portions of said raster pattern area towards said region to be imaged, and in which at least one radiation detector is disposed at the opposite side of said region in the path of said X rays which are transmitted through said collimator passages, wherein the improvement comprises:
   detector support means for supporting said detector at a selected position at said opposite side of said region prior to movement of said X-ray source into position for producing the desired image data, and
   collimator positioning means for defining a predetermined collimator position which is spaced apart from said detector and at which said collimator passages are directed towards said detector, said collimator positioning means being secured to said detector support means in a predetermined spatial relationship to said detector,
   wherein said collimator is secured to said X-ray source and wherein said collimator positioning means includes guide means for receiving and seating at least a forward portion of said collimator as said X-ray source is being brought into position to direct X rays toward said detector.

7. An image region selector as defined in claim 6 further comprising means for blocking seating of said collimator at said collimator positioning means except when said collimator has a predetermined angular orientation relative thereto.

8. An image region selector for a scanning X-ray radiographic system in which an X-ray source and a collimator are disposed at one side of a region to be imaged, the source having a moving X-ray origin point which is swept through a raster pattern area and the point which is swept through a raster pattern area and the collimator having a plurality of passages for transmitting X rays from different portions of said raster pattern area towards said region to be imaged, and in which at least one radiation detector is disposed at the opposite side of said region in the path of said X rays which are transmitted through said collimator passages, wherein the improvement comprises:

detector support means for supporting said detector at a selected position at said opposite side of said region prior to movement of said X-ray source into position for producing the desired image data, and collimator positioning means for defining a predetermined collimator position which is spaced apart from said detector and at which said collimator passages are directed towards said detector, said collimator positioning means being secured to said detector support means in a predetermined spatial relationship to said detector, wherein said collimator positioning means includes an element having an opening shaped to receive the forward end of said X-ray source.

9. An image region selector for a scanning X-ray radiographic system in which an X-ray source and a collimator are disposed at one side of a region to be imaged, the source having a moving X-ray origin point which is swept through a raster pattern area and the collimator having a plurality of passages for transmitting X rays from different portions of said raster pattern area towards said region to be imaged, and in which at least one radiation detector is disposed at the opposite side of said region in the path of said X rays which are transmitted through said collimator passages, wherein said X-ray source includes signal receiving means for receiving detected X-ray signals from said detector, wherein the improvement comprises:

detector support means for supporting said detector at a selected position at said opposite side of said region prior to movement of said X-ray source into position for producing the desired image data, and collimator positioning means for defining a predetermined collimator position which is spaced apart from said detector and at which said collimator passages are directed towards said detector, said collimator positioning means being secured to said detector support means in a predetermined spatial relationship to said detector, and a signal transmitting connector secured to said image region selector in position to engage with said signal receiving means of said X-ray source when said X-ray source is moved into position to direct X rays towards said detector through said collimator.

10. An image region selector as defined in claim 9 further comprising means for blocking seating of said X-ray source at said image region selector unless said signal receiving means of said X-ray source is aligned to engage with said connector.

11. An image region selector for a scanning X-ray radiographic system in which an X-ray source and a collimator are disposed at one side of a region to be imaged, the source having a moving X-ray origin point which is swept through a raster pattern area and the collimator having a plurality of passages for transmitting X rays from different portions of said raster pattern area towards said region to be imaged, and in which at least one radiation detector is disposed at the opposite side of said region in the path of said X rays which are transmitted through said collimator passages, wherein said X-ray source includes signal receiving means for receiving detected X-ray signals from said detector, wherein the improvement comprises:

detector support means for supporting said detector at a selected position at said opposite side of said region prior to movement of said X-ray source into position for producing the desired image data, and collimator positioning means for defining a predetermined collimator position which is spaced apart from said detector and at which said collimator passages are directed towards said detector, said collimator positioning means being secured to said detector support means in a predetermined spatial relationship to said detector, and a signal transmitting connector secured to said image region selector, and a flexible signal conducting cable having means for coupling said signal transmitting connector to said signal receiving means.

12. An image region selector for a scanning X-ray radiographic system in which an X-ray source and a collimator are disposed at one side of a region to be imaged, the source having a moving X-ray origin point which is swept through a raster pattern area and the collimator having a plurality of passages for transmitting X rays from different portions of said raster pattern area towards said region to be imaged, and in which at least one radiation detector is disposed at the opposite side of said region in the path of said X rays which are transmitted through said collimator passages, wherein the improvement comprises:

detector support means for supporting said detector at a selected position at said opposite side of said region prior to movement of said X-ray source into position for producing the desired image data, wherein at least a portion of said detector support means includes a probe shaped for insertion into the mouth of a dental patient, collimator positioning means for defining a predetermined collimator position which is spaced apart from said detector and at which said collimator passages are directed towards said detector, said collimator positioning means being secured to said detector support means in a predetermined spatial relationship to said detector, said image region selector further including bite block means disposed on said probe for enabling support of said image region selector by the teeth of said dental patient.

13. An image region selector as defined in claim 12 wherein an end portion of said probe at which said detector is disposed is angled relative to the portion of said probe at which said bite block means is situated, and wherein said bite block means includes means for enabling selective rotation of said probe relative to said bite block means while said bite block means remains positioned between the teeth of said dental patient.

14. An image region selector as defined in claim 13 wherein said bite block means comprises upper and lower bite block elements between which said detector member is disposed, said bite block elements being formed of at least slightly flexible material enabling said patient to selectively exert clamping pressure on said member through said bite block elements to hold said detector at a selected angular orientation relative to the teeth of said patient.

15. An image region selector for a scanning X-ray radiographic system in which an X-ray source and a collimator are disposed at one side of a region to be imaged, the source having a moving X-ray origin point which is swept through a raster pattern area and the collimator having a plurality of passages for transmitting X rays from different portions of said raster pattern area towards said region to be imaged, and in which at least one radiation detector is disposed at the opposite side of said region in the path of said X rays which are transmitted through said collimator passages, wherein the improvement comprises:

detector support means for supporting said detector at a selected position at said opposite side of said region prior to movement of said X-ray source into position for producing the desired image data, wherein at least a portion of said detector support means includes a probe shaped for insertion into the mouth of a dental patient,     collimator positioning means for defining a predetermined collimator position which is spaced apart from said detector and at which said collimator passages are directed towards said detector, said collimator positioning means being secured to said detector support means in a predetermined spatial relationship to said detector, and,     a removable, replaceable sleeve-like sheath disposed or said probe.

16. An image region selector for a scanning X-ray radiographic system in which an X-ray source and a collimator are disposed at one side of a region to be imaged, the source having a moving X-ray origin point which is swept through a raster pattern area and the collimator having a plurality of passages for transmitting X rays from different portions of said raster pattern area towards said region to be imaged, and in which at least one radiation detector is disposed at the opposite side of said region in the path of said X rays which are transmitted through said collimator passages, wherein said radiation detector has a radiation sensitive area smaller than said raster pattern area of said X-ray source and wherein said passages of said collimator are convergent towards a focal point, wherein the improvement comprises:

detector support means for supporting said detector at a selected position at said opposite side of said region prior to movement of said X-ray source into position for producing the desired image data, and     collimator positioning means for defining a predetermined collimator position which is spaced apart from said detector and at which said collimator passages are directed towards said detector, said collimator positioning means being secured to said detector support means in a predetermined spatial relationship to said detector, and further characterized in that said collimator positioning means has a predetermined spacing from said detector which defines a collimator position at which said small detector intercepts X rays transmitted through each of said plurality of convergent collimator passages.

17. An image region selector component for usage in a dental X-ray system having a scanning X-ray source which produces X rays at a moving origin point which is swept along successive spaced apart scan lines in a raster pattern area and in which X rays are directed through a focusing collimator to a relatively small detector situated on the opposite side of dental structures to be examined, the collimator having a plurality of convergent radiation transmissive passages oriented to transmit X rays from successive points along said scan lines of said raster pattern to said detector, wherein said image region selector component comprises:

a probe member having said detector at a first portion thereof, at least said first portion of said probe member having a configuration suitable for insertion into the mouth of a dental patient, said probe member further having signal transmission means for transmitting X-ray signals from said detector out of said mouth of said patient,     means for supporting said probe member at a selected orientation and position relative to the teeth of said patient prior to the time that said X-ray source is moved into position for irradiation of said teeth, and     a collimator positioner secured to said probe member at a location which establishes a collimator position at which said convergent collimator passages are directed toward said detector.

18. An image region selector as defined in claim 17 wherein said focusing collimator is secured to said scanning X-ray source as a component of the forward end thereof, and wherein said collimator positioner has an opening shaped to receive a forward portion of said X-ray source as said X-ray source is brought into a position at which said convergent collimator passages are directed toward said detector.

19. An image region selector as defined in claim 17 wherein said focusing collimator is a component of said image region selector and is secured to said collimator positioner.

* * * * *